United States Patent [19]

Diana et al.

[11] 4,268,678

[45] May 19, 1981

[54] 4-(ARYLALIPHATIC)ISOXAZOLES

[75] Inventors: Guy D. Diana, Stephentown; Philip M. Carabateas, Schodack, both of N.Y.

[73] Assignee: Sterling Drug Inc., New York, N.Y.

[21] Appl. No.: 72,134

[22] Filed: Sep. 4, 1979

[51] Int. Cl.³ .................... C07D 261/08; A61K 31/42
[52] U.S. Cl. ..................................... 548/247; 424/272; 568/308
[58] Field of Search ......................... 548/247; 424/272

[56] References Cited

U.S. PATENT DOCUMENTS

| | | | |
|---|---|---|---|
| 4,000,150 | 12/1976 | Combon et al. | 548/247 |
| 4,031,246 | 6/1977 | Collins et al. | 424/331 |
| 4,093,736 | 6/1978 | Collins | 424/282 |
| 4,163,057 | 7/1979 | Nadelson | 548/247 |

OTHER PUBLICATIONS

Kochetkov et al., Zhur. Obshchei Chem. 30, 3675–3682 (1960).

*Primary Examiner*—Nicholas S. Rizzo
*Assistant Examiner*—M. C. Eakin
*Attorney, Agent, or Firm*—Thomas L. Johnson; B. Woodrow Wyatt

[57] ABSTRACT

4-(Arylaliphatic)isoxazoles, having antiviral activity, are prepared by reacting with hydroxylamine a diketone of the formula $Ar-Y-CH(CO-R)_2$, wherein Ar is substituted phenyl, Y is $(CH_2)_n$ or $O(CH_2)_n$, and R is lower-alkyl.

9 Claims, No Drawings

4-(ARYLALIPHATIC)ISOXAZOLES

BACKGROUND OF THE INVENTION (a) Field of the Invention

The invention relates to novel 4-(arylaliphatic)-isoxazoles, to the preparation thereof and to compositions and methods for the use thereof as antiviral agents.

(b) Description of the Prior Art

J. C. Collins U.S. Pat. No. 4,093,736, issued June 6, 1978, discloses diketone derivatives useful as pesticidal and antiviral agents having the formula

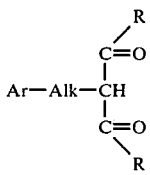

wherein Ar is phenyl or substituted phenyl, Alk is alkylene of 4–10 carbon atoms and R is lower-alkyl.

J. C. Collins and G. D. Diana U.S. Pat. No. 4,031,246, issued June 21, 1977, discloses diketone derivatives useful as pesticidal and antiviral agents having the formula

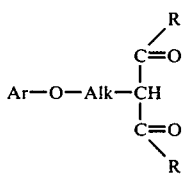

wherein Ar is phenyl or substituted phenyl, Alk is alkylene of 3–10 carbon atoms and R is lower-alkyl.

The compounds of the above-noted U.S. Pat. Nos. 4,093,736 and 4,031,246 are intermediates in the preparation of the compounds of the instant invention.

Kochetkov et al., Zhur. Obshchei Chem. 30, 3675 (1960) discloses 4-benzyl-3,5-dimethylisoxazole. No biological properties are reported.

SUMMARY OF THE INVENTION

In a composition of matter aspect, the invention relates to 4-(arylalkyl)isoxazoles and 4-(aryloxyalkyl)isoxazoles, said isoxazoles having the formula

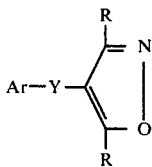

wherein Ar is phenyl substituted by one or two substituents selected from the group consisting of halogen, lower-alkoxy, nitro and hydroxy; Y is $(CH_2)_n$ or $O(CH_2)_n$ where n is an integer from 1 to 8; and R is lower-alkyl.

In a further composition of matter aspect, the invention relates to a composition for combatting viruses which comprises an antivirally effective amount of at least one compound of the above Formula I in admixture with a suitable carrier or diluent.

In a process aspect, the invention relates to a process for preparing a compound of Formula I which comprises reacting with hydroxylamine a diketone of the formula

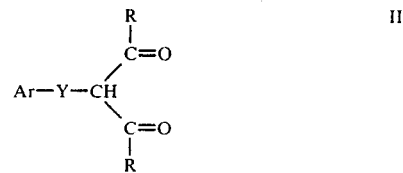

where Ar, Y and R have the meanings given above.

In a further process aspect, the invention relates to a method for combatting viruses which comprises contacting the locus of said viruses with an antivirally effective amount of at least one compound of Formula I.

DETAILED DESCRIPTION INCLUSIVE OF PREFERRED EMBODIMENTS

In the compounds of Formula I, when the phenyl ring of Ar is substituted by lower-alkoxy, the lower-alkoxy group or groups preferably have from one to four carbon atoms; and when halogen substituents are present they can be any of the four common halogens, fluoro, chloro, bromo or iodo. The carbon chain of R can be staight or branched and preferably has from one to four carbon atoms.

The compounds of Formula I are prepared by interacting a diketone of Formula II above with hydroxylamine or an acid-addition salt thereof. The reaction takes place in an inert solvent at a temperature between about 50° and 150° C. The nature of the inert solvent is not critical, although preferred solvents are lower-alkanols, such as methanol or ethanol, acetic acid and pyridine. Stoichiometrically equivalent amounts of diketone and hydroxylamine may be used, although a slight excess of hydroxylamine is generally employed.

The intermediate diketones of Formula II are a known class of compounds disclosed in U.S. Pat. Nos. 4,031,246 and 4,093,736.

The structures of the compounds of the invention were established by the modes of synthesis, by elementary analysis, and by infrared and nuclear magnetic resonance spectral determinations.

Biological evaluation of the compounds of the invention has shown that they possess antiviral activity. They are useful in combatting viruses present on inanimate surfaces as well as viral infections in animal organisms. The in vitro testing of the compounds of the invention against herpes simplex virus type 2 has showed that they inhibited viral growth at minimum concentrations (MIC) ranging from about 1.5 to about 50 micrograms per milliliter. The MIC values were determined by standard serial dilution procedures.

The antiviral compositions are formulated by preparing a dilute solution or suspension in an organic or aqueous-organic medium, for example ethyl alcohol, acetone, dimethyl sulfoxide, and the like; and are applied to the locus to be disinfected by conventional means such as spraying, swabbing or immersing. Alternatively, the compounds can be formulated as ointments or creams by incorporating them in conventional ointment or cream bases, such as alkylpolyether alcohols, cetyl alcohol, stearyl alcohol and the like; as jellies by incorporating them in conventional jelly bases such as glycerin and tragacanth; or as aerosol sprays or foams. The antivirally effective component of the composition is present in a concentration of between about 0.7 part per million and about 5 percent by weight, depending upon the chemical species used, the object to be treated and the type of formulation employed. For disinfection of inanimate surfaces with aqueous or aqueous-organic solutions, concentrations in the lower part of the range are effective. For topical application in medical or veterinary use in the form of ointment, cream, jelly or aerosol, concentrations in the upper part of the range are preferred.

The following examples will further illustrate the invention.

EXAMPLE 1

4-[6-(2-Chloro-4-methoxyphenoxy)hexyl]-3,5-diethylisoxazole [I; Ar is 2-Cl-4-CH$_3$OC$_6$H$_3$, Y is O(CH$_2$)$_6$, R is C$_2$H$_5$].

A mixture of 18.5 g. (0.050 mole) of 4-[6-(2-chloro-4-methoxyphenoxy)hexyl]-3,5-heptanedione, 3.82 g. (0.055 mole) of hydroxylamine hydrochloride and 150 ml. of pyridine was stirred on a steam bath for one four and allowed to stand at room temperature for two days. The reaction mixture was concentrated in vacuo, and the semi-solid residue was partitioned between methylene dichloride and water. The methylene dichloride extract was washed with water and dried over anhydrous magnesium sulfate. The methylene dichloride was removed in vacuo and the residual product was chromatographed on 360 g. of silica. The chromatogram was eluted with a 3:1 mixture of n-hexane and ethyl acetate, five one liter fractions being collected. The material in the first fraction, shown to be a homogeneous product by thin layer chromatography, was isolated by removal of the solvent to give 10.1 g. (55%) of 4-[6-(2-chloro-4-methoxyphenoxy)hexyl]-3,5-diethylisoxazole as a yellow oil.

Anal. Calcd. for C$_{28}$H$_{28}$ClNO$_3$: C, 65.65; H, 7.71; N, 3.83. Found: C, 65.63; H, 7.78; N, 3.80.

4-[6-(2-Chloro-4-methoxyphenoxy)hexyl]-3,5-diethylisoxazole when tested in vitro against herpes simplex virus type 2 showed antiviral activity at a minimal inhibitory concentration (MIC) of 6 micrograms per milliliter ($\mu$g/ml).

EXAMPLE 2

(a) 4-[(4-Methylphenyl)methyl]-3,5-heptanedione

To a suspension of 2.78 g. (0.35 mole) of lithium hydride in 250 ml. of dimethylformamide was added dropwise over a period of 30 min. a solution of 44.6 g. (0.35 mole) of 3,5-heptanedione in 50 ml. of dimethylformamide. Thereafter, 42.5 g. (0.3 mole) of α-chloro-p-xylene was added all at once, and the reaction mixture was stirred at 70°–75° C. for 22 hours. The mixture was then poured into a solution of 100 ml. of concentrated hydrochloric acid in one liter of water. The product was extracted with methylene dichloride and the extracts washed with water and dried over anhydrous magnesium sulfate. The solution was concentrated in vacuo and the residue distilled twice, at 90°–106° C. (0.03 mm.) and 103°–105° C. (0.03 mm.) to give 41.8 g. of 4-[(4-methylphenyl)methyl]-3,5-heptanedione.

(b) 3,5-Diethyl-4-[(4-methylphenyl)methyl]isoxazole [I; Ar is 4-CH$_3$C$_6$H$_4$, Y is CH$_2$, R is C$_2$H$_5$]

A mixture of 41.8 g. of 4-[(4-methylphenyl)methyl]-3,5-heptanedione from part (a) above, 12.5 g. of hydroxylamine hydrochloride and 100 ml. of pyridine was stirred at reflux temperature for three hours and then allowed to stand at room temperature for two days. The reaction mixture was concentrated in vacuo, and the residue was partitioned between dilute aqueous hydrochloric acid and methylene dichloride. The latter solution was washed with water, dried over anhydrous magnesium sulfate and concentrated in vacuo. The product was distilled at 101°–103° C. (0.2 mm.) to give 8.1 g. of 3,5-diethyl-4-[(4-methylphenyl)-methyl]isoxazole; MIC=1.5 $\mu$g/ml (herpes 2).

Anal. Calcd. for C$_{15}$H$_{19}$NO: C, 78.56; H, 8.35; N, 6.11. Found: C, 78.67; H, 8.44; N, 5.98.

EXAMPLE 3

(a) 4-(4-Methoxyphenylmethyl)-3,5-heptanedione was prepared from 62.5 g. of p-methoxybenzyl chloride and the lithium salt from 57.5 g. of 3,5-heptanedione according to the procedure of Example 2, part (a), and was obtained in the form of a pale yellow liquid, b.p. 138°–139° C. (0.03 mm.); yield 80.0 g.

(b) 3,5-Diethyl-4-[(4-methoxyphenyl)methyl]isoxazole [I; Ar is 4-CH$_3$OC$_6$H$_4$, Y is CH$_2$, R is C$_2$H$_5$] was prepared from 41.1 g. of 4-(4-methoxyphenylmethyl)-3,5-heptanedione and 12.0 g. of hydroxylamine hydrochloride in 100 ml. of pyridine according to the procedure of Example 2, part (b), and was obtained in the form of a colorless oil, b.p. 145°–146° C. (0.1 mm.); MIC=25 $\mu$g/ml (herpes 2).

Anal. Calcd. for C$_{15}$H$_{19}$NO$_2$: C, 73.44; H, 7.81; N, 5.71. Found: C, 73.43; N, 7.67; N, 5.55.

EXAMPLE 4

(a) 4-[(2-Chloro-4-methoxyphenyl)methyl]-3,5-heptanedione was prepared from 48.9 g. of 2-chloro-4-methoxybenzyl bromide and the lithium salt from 32 g. of 3,5-heptanedione according to the procedure of Example 2, part (a), and was obtained in the form of a yellow oil, b.p. 143°–144° C. (0.03 mm.); yield 51.1 g.

(b) 4-[(2-Chloro-4-methoxyphenyl)methyl]-3,5-diethylisoxazole [I; Ar is 2-Cl-4-CH$_3$OC$_6$H$_3$, Y is CH$_2$, R is C$_2$H$_5$] was prepared from 30.9 g. of 4-[(2-chloro-4-methoxyphenyl)methyl]-3,5-heptanedione and 7.96 g. of hydroxylamine hydrochloride in 65 ml. of pyridine according to the procedure of Example 2, part (b), and was obtained in the form of a pale yellow oil, b.p. 144°–147° C. (0.08 mm.); yield 21.6 g.; MIC=12 $\mu$g/ml (herpes 2).

Anal. Calcd. for C$_{15}$H$_{18}$ClNO$_2$: C, 64.39; H, 6.48; N, 5.01; Cl, 12.67. Found: C, 64.67; H, 6.51; N, 4.99; Cl, 12.40.

EXAMPLE 5

3,5-Diethyl-4-[6-(4-methoxy-2-nitrophenoxy)hexyl]isoxazole [I; Ar is 2-O$_2$N-4-CH$_3$OC$_6$H$_3$, Y is O(CH$_2$)$_6$, R is C$_2$H$_5$] was prepared from 10.0 g. of 4-[6-(4-methoxy-2-nitrophenoxy)hexyl]-3,5-heptanedione and 2.0 g. of hydroxylamine hydrochloride in 40 ml. of pyridine according to the procedure of Example 2, part (b), and was obtained in the form of a yellow oil, b.p. 200°–205° C. (0.02 mm.); yield 7.5 g.; MIC=3 $\mu$g/ml (herpes 2).

Anal. Calcd. for C$_{20}$H$_{28}$N$_2$O$_5$: C, 63.81; H, 7.50; N, 7.44. Found: C, 63.81; H, 7.50; N, 7.24.

EXAMPLE 6

4-[6-(4-Bromophenoxy)hexyl]-3,5-diethylisoxazole [I; Ar is 4-BrC$_6$H$_4$, Y is O(CH$_2$)$_6$, R is C$_2$H$_5$] was prepared from 10.0 g. of 4-[6-(4-bromophenoxy)hexyl]-3,5-heptanedione and 2.0 g. of hydroxylamine hydrochloride in 40 ml. of pyridine according to the procedure of Example 2, part (b), and was obtained in the form of a pale yellow oil, b.p. 190°–195° C. (0.001 mm.); yield 7.3 g.; MIC=12 μg/ml (herpes 2).

Anal. Calcd. for C$_{19}$H$_{26}$BrNO$_2$: C, 60.00; H, 6.89; N, 3.68; Br, 21.01. Found: C, 60.19; H, 6.77; N, 3.65; Br, 21.21.

EXAMPLE 7

4-[4-(2-Chloro-4-methoxyphenoxy)butyl]-3,5-diethylisoxazole [I; Ar is 2-Cl-4-CH$_3$OC$_6$H$_3$, Y is O(CH$_2$)$_4$, R is C$_2$H$_5$] was prepared from 16.2 g. of 4-[4-(2-chloro-4-methoxyphenoxy)butyl]-3,5-heptanedione and 3.3 g. of hydroxylamine hydrochloride in 65 ml. of pyridine according to the procedure of Example 2, part (b), and was obtained in the form of a yellow oil, b.p. 180°–190° C. (0.1 mm.); yield 9.3 g.; MIC=6 μg/ml (herpes 2).

Anal. Calcd. for C$_{18}$H$_{24}$ClNO$_3$: C, 63.99; H, 7.16; Cl, 10.49. Found: C, 63.85; H, 7.18; Cl, 10.36.

EXAMPLE 8

4-[7-(2-Chloro-4-methoxyphenoxy)heptyl]-3,5-diethylisoxazole [I; Ar is 2-Cl-4-CH$_3$OC$_6$H$_3$, Y is O(CH$_2$)$_7$, R is C$_2$H$_5$] was prepared from 19.2 g. of 4-[7-(2-chloro-4-methoxyphenoxy)heptyl]-3,5-heptanedione, 5 g. of hydroxylamine hydrochloride and 5.0 g. of triethylamine in 100 ml. of absolute ethanol. The reaction mixture was stirred at reflux for 24 hrs., then concentrated in vacuo and partitioned between water and methylene dichloride. The material obtained from the methylene dichloride extracts was chromatographed on silica and eluted with a 4:1 mixture of hexane and ethyl acetate. The resulting product was distilled twice in vacuo to give 5.2 g. of 4-[7-(2-chloro-4-methoxyphenoxy)-heptyl]-3,5-diethylisoxazole, pale yellow oil, b.p. 180°–190° C. (0.01 mm.); MIC=>25 μg/ml (herpes 2).

Anal. Calcd. for C$_{21}$H$_{30}$ClNO$_3$: C, 66.39; H, 7.96; N, 3.69. Found: C, 66.83; H, 8.02; N, 3.27.

EXAMPLE 9

(a) 4-[(4-Hydroxyphenyl)methyl]-3,5-heptanedione was prepared by hydrogenolysis, in ethanol solution in the presence of 10% palladium-on-carbon catalyst, of 17.0 g. of 4-[(4-benzyloxy-phenyl)methyl]-3,5-heptanedione, m.p. 44°–54° C., in turn prepared from 4-benzyloxybenzyl chloride and the lithium salt of 3,5-heptanedione. The product thus obtained was recrystallized from methanol to give 4.6 g. of 4-[(4-hydroxyphenyl)methyl]-3,5-heptanedione, m.p. 95°–96° C.

(b) 3,5-Diethyl-4-[(4-hydroxyphenyl)methyl]isoxazole [I; Ar is 4-HOC$_6$H$_4$, Y is CH$_2$, R is C$_2$H$_5$] can be prepared by reacting 4-[(4-hydroxyphenyl)methyl]-3,5-heptanedione with hydroxylamine hydrochloride in pyridine according to the procedure of Examples 1 or 2.

It is further contemplated that the following compounds:

4-[6-(4-hydroxyphenyl)hexyl]-3,5-heptanedione
4-[6-(3,4-dihydroxyphenyl)hexyl]-3,5-heptanedione
4-[6-(4-hydroxyphenoxy)hexyl]-3,5-heptanedione
4-[6-(2-fluorophenoxy)hexyl]-3,5-heptanedione
4-[6-(3-iodophenoxy)hexyl]-3,5-heptanedione
3-[8-(2-chloro-4-methoxyphenoxy)octyl]-2,4-pentanedione
and 4-[6-(2-chloro-4-methoxyphenoxy)hexyl]-2,2,6,6-tetramethyl-3,5-heptanedione can be reacted with hydroxylamine in accordance with the procedures described above to give, respectively:

3,5-diethyl-4-[6-(4-hydroxyphenyl)hexyl]isoxazole [I; Ar is 4-HOC$_6$H$_4$, Y is (CH$_2$)$_6$, R is C$_2$H$_5$]
3,5-diethyl-4-[6-(3,4-dihydroxyphenyl)hexyl]isoxazole [I; Ar is 3,4-(HO)$_2$C$_6$H$_3$, Y is (CH$_2$)$_6$, R is C$_2$H$_5$]
3,5-diethyl-4-[6-(4-hydroxyphenoxy)hexyl]isoxazole [I; Ar is 4-HOC$_6$H$_4$, Y is O(CH$_2$)$_6$, R is C$_2$H$_5$]
3,5-diethyl-4-[6-(2-fluorophenoxy)hexyl]isoxazole [I; Ar is 2-FC$_6$H$_4$, Y is O(CH$_2$)$_6$, R is C$_2$H$_5$]
3,5-diethyl-4-[6-(3-iodophenoxy)hexyl]isoxazole [I; Ar is 3-IC$_6$H$_4$, Y is O(CH$_2$)$_6$, R is C$_2$H$_5$]
4-[8-(2-chloro-4-methoxyphenoxy)octyl]-3,5-dimethylisoxazole [I; Ar is 2-Cl-4-CH$_3$OC$_6$H$_3$, Y is O(CH$_2$)$_8$, R is CH$_3$]
and 4-[6-(2-chloro-4-methoxyphenoxy)hexyl]-3,5-ditertiary-butylisoxazole [I; Ar is 2-Cl-4-CH$_3$OC$_6$H$_3$, Y is O(CH$_2$)$_6$, R is C(CH$_3$)$_3$].

We claim:

1. A compound of the formula:

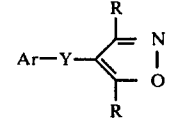

wherein Ar is phenyl substituted by one or two substituents selected from the group consisting of halogen, lower-alkoxy, nitro and hydroxy;
Y is (CH$_2$)$_n$ or O(CH$_2$)$_n$ where n is an integer from 1 to 8; and R is lower-alkyl.

2. 3,5-Diethyl-4-[(4-methoxyphenyl)methyl]isoxazole, according to claim 1.

3. 3,5-Diethyl-4-[6-(4-methoxy-2-nitrophenoxy)hexyl]-isoxazole, according to claim 1.

4. 3,5-Diethyl-4-[6-(4-bromophenoxy)hexyl]isoxazole, according to claim 1.

5. A compound according to claim 1 wherein Ar is 2-chloro-4-methoxyphenyl.

6. 4-[6-(2-Chloro-4-methoxyphenoxy)hexyl]-3,5-diethylisoxazole, according to claim 5.

7. 4-[(2-Chloro-4-methoxyphenyl)methyl]-3,5-diethyl-isoxazole, according to claim 5.

8. 4-[4-(2-Chloro-4-methoxyphenoxy)butyl]-3,5-diethylisoxazole, according to claim 5.

9. 3,5-Diethyl-4-[(4-methylphenyl)methyl]isoxazole.

* * * * *